US012106679B2

(12) United States Patent
Katti et al.

(10) Patent No.: US 12,106,679 B2
(45) Date of Patent: Oct. 1, 2024

(54) COMPLIANT MECHANISM FOR SIMULATING ENDOSCOPY

(71) Applicant: INDIAN INSTITUTE OF SCIENCE, Bangalore (IN)

(72) Inventors: Anirudh Katti, Bangalore (IN); Shanthanu Chakravarthy, Bangalore (IN); Gondi Kondaiah Ananthasuresh, Bangalore (IN)

(73) Assignee: Indian Institute of Science, Bangalore (IN)

( * ) Notice: Subject to any disclaimer, the term of this patent is extended or adjusted under 35 U.S.C. 154(b) by 10 days.

(21) Appl. No.: 16/525,968

(22) Filed: Jul. 30, 2019

(65) Prior Publication Data
US 2021/0035470 A1 Feb. 4, 2021
US 2022/0383776 A9 Dec. 1, 2022

Related U.S. Application Data

(63) Continuation of application No. PCT/IB2018/050598, filed on Jan. 31, 2018.

(30) Foreign Application Priority Data

Feb. 1, 2017 (IN) .............................. 201741003733

(51) Int. Cl.
G09B 23/28 (2006.01)
A61B 1/00 (2006.01)
G09B 9/00 (2006.01)

(52) U.S. Cl.
CPC ........ G09B 23/285 (2013.01); A61B 1/00131 (2013.01); G09B 9/00 (2013.01)

(58) Field of Classification Search
CPC ........ G09B 23/28; G09B 23/285; G09B 9/00; G09B 23/30; G09B 23/32; A61B 1/00131
See application file for complete search history.

(56) References Cited

U.S. PATENT DOCUMENTS 5,704,791 A * 1/1998 Gillio ...................... G09B 5/14
434/262
5,800,179 A * 9/1998 Bailey ................... A61B 34/76
434/262

(Continued)

FOREIGN PATENT DOCUMENTS

CN  1293801 A   5/2001
EP  2512577    10/2012

(Continued)

OTHER PUBLICATIONS

Baldwin Po Man Yeung & Terence Gourlay, A technical review of flexible endoscopic multitasking platforms, Int'l J. of Surgery, vol. 10 No. 7, pp. 345-354, doi:10.1016/j.ijsu.2012.05.009 (May 26, 2012).

(Continued)

*Primary Examiner* — Timothy A Musselman
(74) *Attorney, Agent, or Firm* — David E. Boundy; Potomac Law Group, PLLC

(57) ABSTRACT

The present disclosure discloses a compliant mechanism (100) for application of radial resistance on a simulation endoscope (101). The mechanism (100) comprises a support plate (102), a ring member (103) rotatably mounted on the support plate (102) and a plurality of flexible beam assemblies (104) configured in an inner circumference of the ring member (103). The plurality of flexible beam assemblies (104) comprises a first beam (104a) connectable to the ring member (103) and a second beam (104b) connectable to the support plate (102), the circular motion of at least one of the support plate (102) and the ring member (103), relative to each other, moves the plurality of flexible beam assemblies (104) radially inward and radially outward to selectively apply radial resistance on the simulation endoscope (101). The complaint mechanism (100) of present disclosure are (Continued)

joint less mechanisms which are free from backlash and friction in joints.

13 Claims, 6 Drawing Sheets

(56) References Cited

U.S. PATENT DOCUMENTS

| | | | | |
|---|---|---|---|---|
| 6,024,576 A | * | 2/2000 | Bevirt | G05G 9/04 |
| | | | | 345/158 |
| 6,863,536 B1 | | 3/2005 | Fisher | |
| 7,455,523 B2 | * | 11/2008 | Hendrickson | G09B 23/285 |
| | | | | 434/262 |
| 2001/0016804 A1 | | 8/2001 | Cunningham | |
| 2003/0068607 A1 | * | 4/2003 | Gregorio | A61B 34/71 |
| | | | | 434/262 |
| 2004/0048230 A1 | | 3/2004 | Alexander | |
| 2005/0064378 A1 | | 3/2005 | Toly | |
| 2009/0130643 A1 | * | 5/2009 | Cusano | G09B 23/28 |
| | | | | 434/262 |
| 2015/0325147 A1 | * | 11/2015 | Johansson | G09B 23/28 |
| | | | | 434/262 |
| 2021/0128258 A1 | * | 5/2021 | Quaid | A61B 34/70 |

FOREIGN PATENT DOCUMENTS

| | | |
|---|---|---|
| IN | 3439-CHE-2014 | 7/2014 |
| IN | 201741003733 A | 2/2017 |
| WO | WO1999/038141 A1 | 7/1999 |
| WO | WO2011/027329 | 3/2011 |
| WO | WO2016/005959 | 7/2015 |
| WO | WO2018/142297 | 8/2018 |

OTHER PUBLICATIONS

PCT/IB2015/055251, Search Report and Written Opinion (dated Oct. 28, 2015).
PCT/IB2015/055251, International Preliminary Report on Patentability (dated Nov. 14, 2016).
PCT/IB2018/050598, Search Report and Written Opinion (dated Apr. 10, 2018).
PCT/IB2018/050598, International Preliminary Report on Patentability (dated Jul. 4, 2019).

* cited by examiner

COMPLIANT MECHANISM FOR SIMULATING ENDOSCOPY

TECHNICAL FIELD

This application is a U.S. National Phase entry International Application PCT/IB2018/050598, which claims priority from India application 201741003733, all of which are incorporated by reference.

The present disclosure generally relates to a field of bio-medical devices. Particularly but not exclusively, the present disclosure relates to endoscopy simulation device. Further embodiments of the disclosure disclose a compliant mechanism for application of radial resistance on a simulation endoscope during endoscopy simulation.

BACKGROUND OF THE DISCLOSURE

Endoscopy is a minimally invasive procedure where a flexible tube is inserted through the digestive tract of a subject for medical examination, and also for surgical interventions. Medical practitioners, practicing endoscopy screen the subject using a tool called endoscope. Upper Gastrointestinal (GI) endoscopy is one of the types of endoscopy, where the endoscope is inserted through the mouth of the subject into the GI tract. This type of endoscopy is complex in procedure and may be carried out only by skilled clinicians or medical practitioners. Thus, clinicians or medical practitioners planning to practice endoscopy should undergo rigorous and extensive training on the simulator before they try endoscopy on human subjects which necessitates the need of endoscopy simulators. Conventionally, endoscopic simulators have been made in the form of physical models which lack practicality and it provides low chances of variations.

Considering the above factors, computer based training models and various solutions including Virtual Reality (VR) for training the doctors have been proposed. In one such proposal, a clinical endoscope comprising an inlet for insertion, a sensor arrangement to detect movement of the instrument, and a controller to generate a virtual image of an endoscopic operation based on the movement of the instrument is disclosed.

Further, a device for simulating endoscopy is known in the art. Such device includes an endoscopic haptic interface with a friction roller which is connected to a motor for transmission of torque. Further, there is an axial brake, to block axial movement of the endoscope and allows rotation of the endoscope. The brake has two pairs of brake rollers, where one roller pair is movable relative to the other roller pair. The device consists of another friction roller mounted on the tube via a lever, which is actuated by a spring for insertion of endoscopes of different sizes and for providing contact force on the endoscope of the rollers.

However, the existing art including VR-based training systems fail to provide an immersive training environment. Further, simulation of resistance offered on the endoscope during insertion through throat is one of the critical steps in endoscopic training. The known arts disclose the use of a rigid-body mechanisms for simulation of such resistance during endoscopy simulation. However, the use rigid body mechanism in the endoscope simulation device have drawbacks such as friction in joints and may cause wear and tear. Further, the use of rigid body mechanism in the endoscope may not give a user the actual feel of using an endoscope in reality.

The present disclosure is proposed to overcome one or more limitations stated above.

SUMMARY OF THE DISCLOSURE

One or more shortcomings of the prior arts are overcome by a mechanism as claimed and additional advantages are provided through the provision of the mechanism as claimed in the present disclosure. Additional features and advantages are realized through the techniques of the present disclosure. Other embodiments and aspects of the disclosure are described in detail herein and are considered a part of the disclosure.

In one non-limiting embodiment of the disclosure, a compliant mechanism for application of radial resistance on a simulation endoscope is disclosed. The mechanism comprising a support plate, a ring member rotatably mounted on the support plate and a plurality of flexible beam assemblies configured in an inner circumference of the ring member. The plurality of flexible beam assemblies comprises a first beam connectable to the ring member and a second beam connectable to the support plate. The circular motion of at least one of the support plate and the ring member, relative to each other, moves the plurality of flexible beam assemblies radially inward and radially outward to selectively apply radial resistance on the simulation endoscope.

In an embodiment of the disclosure, radial resistance is applied on the simulation endoscope when the plurality of flexible beam assemblies moves radially inward.

In an embodiment of the disclosure, the ring member is mounted on the support plate through a bearing, wherein, an outer race of the bearing is fixed to the support plate and an inner race of the bearing accommodates the ring member.

In an embodiment of the disclosure, free ends of the first beam and the second beam of each of the plurality of flexible beam assemblies are interconnected to form a support region. The mechanism comprises a gripping pad provisioned on the support region.

In an embodiment of the disclosure, the plurality of flexible beam assemblies are equidistantly spaced to form a circular supporting region in the ring member.

In an embodiment of the disclosure, the mechanism comprises an actuator coupled to the ring member, the actuator is configured to impart the circumferential actuation to ring member. The circumferential actuation causes rotary movement of the ring member.

In an embodiment of the disclosure, the radially outward movement of at least one of the plurality of flexible beam assemblies imparts circumferential motion to the ring member.

In an embodiment of the disclosure, the mechanism comprises a sensor coupled to the actuator. The sensor is configured to sense the magnitude of radially outward movement of the at least one of the plurality of flexible beam assemblies.

It is to be understood that the aspects and embodiments of the disclosure described above may be used in any combination with each other. Several of the aspects and embodiments may be combined together to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING FIGURES

The novel features and characteristic of the disclosure are set forth in the appended claims. The disclosure itself, however, as well as a preferred mode of use, further objectives, and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

Figure 1:
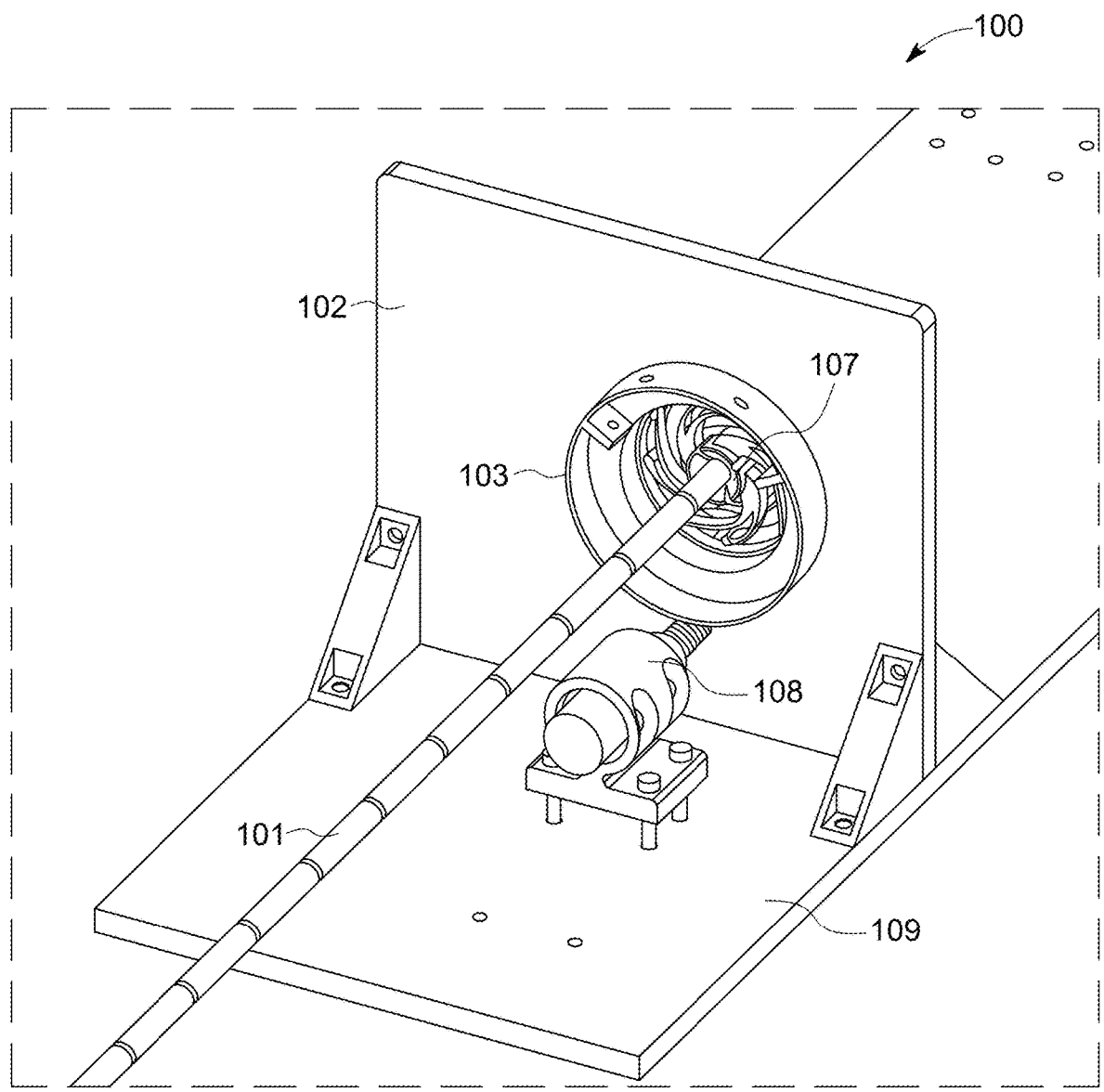
FIG. 1 illustrates a perspective view of a compliant mechanism for applying radial resistance on a simulation endoscope.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other device for carrying out the same purposes of the present disclosure. It should also be realized by those skilled in the art that such equivalent constructions do not depart from the scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

While the disclosure is susceptible to various modifications and alternative forms, specific embodiment thereof has been shown by way of example in the drawings and will be described in detail below. It should be understood, however, that it is not intended to limit the disclosure to the particular forms disclosed, but on the contrary, the disclosure is to cover all modifications, equivalents, and alternatives falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure relate to a compliant mechanism for application of radial resistance on a simulation endoscope.

A compliant mechanism may transmit and transform motion/force using elastic deformation. Compliant mechanisms provide an advantage over conventional rigid body mechanisms as they are free from backlash, play, and friction in joints. With these features, compliant mechanism may be used in medical applications in medical devices such as hemostats, forceps, etc. The mechanism may be worked with all the standard endoscopes.

A compliant mechanism for application of radial resistance on a simulation endoscope may comprise a support plate to provide support to different components of the mechanism. Further, there is a ring member in the mechanism which is rotatably mounted on the support plate. The ring member may be circumferentially actuated to transmit motion or force to elastic members of the compliant mechanism. The elastic members may be a plurality of flexible beam assemblies configured in an inner circumference of the ring member. In one embodiment, the plurality of flexible beam assemblies comprises a first beam and a second beam. The first beam may be connectable to the ring member and a second beam connectable to the support plate. The circumferential actuation of the ring member moves the plurality of flexible beam assemblies radially inward and radially outward to selectively apply radial resistance on the simulation endoscope. Application of the radial resistance on the simulation endoscope may be required to simulate the force condition when the endoscope encounters sphincter muscle in a body of the subject. The mechanism, thus by providing haptic feedback, assists in training for insertion of an endoscope into esophagus instead of the trachea. The ring member of the mechanism may be mounted on the support plate through a bearing. The outer race of the bearing is fixed to the support plate and an inner race of the bearing accommodates the ring member.

Further, free ends of the each of plurality of flexible beam assemblies may be interconnected to form a support region. The free ends of the plurality of flexible beam assemblies are also provided with gripping pads, to support simulation endoscope entering the support region. The mechanism may comprise an actuator coupled to the ring member to impart circumferential actuation to the ring member. The circumferential actuation to the ring member rotates the ring member which causes radially inward movement of the plurality of flexible beam assemblies. The mechanism is also configured with a sensor coupled to the actuator. The sensor is configured to sense the magnitude of displacements of a plurality of flexible beam assemblies when they move in a radially outward direction. Thus, the complaint mechanism may be capable of achieving reversible actuation between circumferential and radial directions to provide continuous haptic feedback during the simulation.

Henceforth, the present disclosure is explained with the help of figures of the compliant mechanism. However, such example embodiments should not be construed as limitations of the present disclosure. A person skilled in the art can envisage various such embodiments without deviating from the scope of the present disclosure.

FIG. 1 illustrates a perspective view of a compliant mechanism (100) for applying radial resistance on a simulation endoscope (101). The compliant mechanism (100) provides haptic feedback to a user during simulation of endoscopy. The mechanism (100) may be configured to apply radial resistance on simulation endoscope, to simulate the condition of encountering sphincter muscle during insertion of the endoscope in the throat of the human body. The complaint mechanism (100) may apply a resistive force on the simulation endoscope (101) radially to simulate the insertion of simulation endoscope into the sphincter muscle such as esophagus or food pipe. The complaint mechanism (100) may be used in a device for simulating endoscopy for training the practitioners. The compliant mechanism (100) may be configured to transmit and transform motion/force using elastic deformation. The motion or force using elastic deformation is transmitted to a plurality of flexible beam assemblies (104) configured in an inner circumference of a ring member (103) of the mechanism (100). The mechanism (100) comprises a support plate (102) to provide support to various components of the mechanism (100). The support plate (102) may be configured as an upright vertical plate to provide support to other components of the mechanism (100). The support plate (102) may be made of a metallic material or a polymeric material of sufficient strength and pre-defined thickness. As shown in FIG. 1, the support plate (102) is further adjoined to a base plate (109) configured horizontally to provide support to components to be mounted on ground level. The mechanism (100) comprises a ring member (103) rotatably mounted on the support plate (102). The ring member (103) may be made of a polymeric material to serve its purpose. However, one should not construe type of material of the ring member (103) as a limitation, as the ring member (103) may be made of materials other than polymeric material. The term ring member (103) may be a circular ring-like structure having a predetermined thickness and diameter.

The compliant mechanism (100) further comprises a plurality of flexible beam assemblies (104) configured in an inner circumference of the ring member (103). In an embodiment, the flexible beam assemblies (104) may be made of a material such as polymeric material, as that of the ring member (103), where the beam assemblies (104) are configured as an integral part of the ring member (103). In another embodiment, the plurality of flexible beam assemblies (104) may be made of a material different from the ring member (103). The beam assemblies (104) are made flexible such that the beam assemblies (104) move radially inward and outward exhibiting elastic deformation to transmit force to the simulation endoscope. In some embodiments of the disclosure, each of the plurality of flexible beam assemblies (104) further comprises a first beam (104a) and a second beam (104b). The first beam (104a) is connectable to the ring member (103) and the second beam (104b) is connectable to the support plate (102).

Further, the mechanism (100) comprises an actuator (108) to actuate the ring member (103). The actuator (108) may be a motor, or a hydraulic or a pneumatic actuator. The actuator (108) may impart circumferential motion to the ring member (103). In an embodiment, the output shaft of the actuator (108) may be coupled to a capstan roller which is in turn coupled to the ring member (103) to transmit power from the actuator (108) to the ring member (103) to apply circumferential motion to the ring member (103). The ring member (103) further converts this circumferential motion into radial motion of the plurality of flexible beam assemblies (104).

The plurality of flexible beam assemblies (104) may be configured to apply radial resistance on the endoscope (101) to simulate the condition of encountering sphincter muscle such as but not limited to food pipe in the throat.

Figure 2:
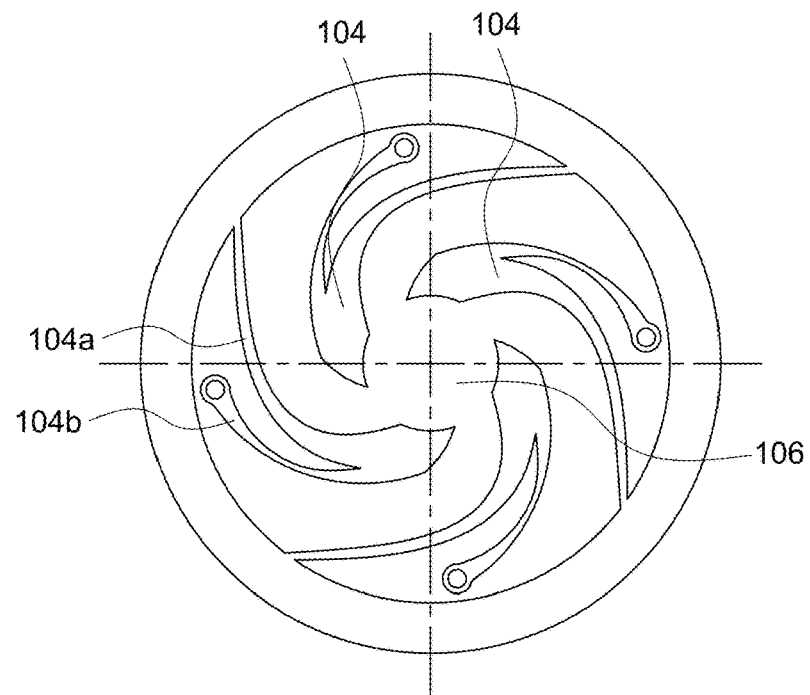
FIG. 2 illustrates a front view of the ring member and flexible beam assemblies of the complaint mechanism of FIG. 1.

Referring now to FIG. 2, which illustrates a front view of the ring member (103) and the flexible beam assemblies (104) of the complaint mechanism (100). The ring member (103) constitutes a part of the mechanism (100) which may be configured to transmit input motion or force to the plurality of flexible beam assemblies (104). The plurality of flexible beam assemblies (104) further offers resistive force on the simulation endoscope (101) during its insertion into the throat. The number of flexible beam assemblies (104) in the mechanism (100) may be at least two in number to offer resistive force on the simulation endoscope (101).

Figure 3:
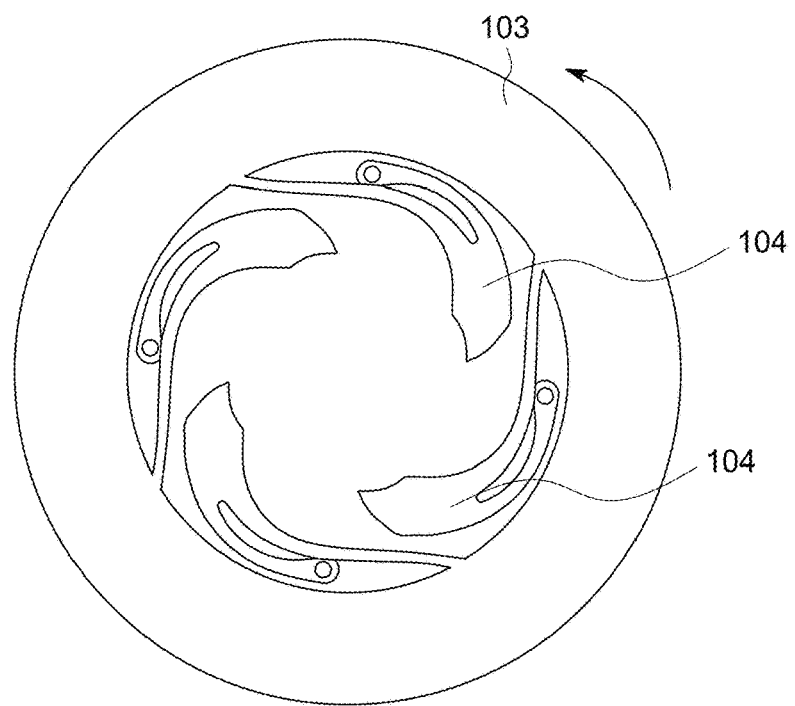
FIG. 3 and FIG. 6 illustrate front view of the ring member and the flexible beam assemblies of complaint mechanism of FIG. 2 showing the movement of flexible beams in radially inward and radially outward directions respectively.

As shown in FIG. 3, when the circumferential motion or force is applied on the ring member (103) through the actuator (108), the ring member (103) rotates in one direction for example in counter clock-wise direction. The rotational motion of the ring member (103) results in radial inward movement of the plurality of flexible beam assemblies (104). The radial inward motion of the plurality of flexible beam assemblies (104) is achieved by fixing the second beam (104b) of each of the plurality of flexible beam assemblies (104) to the support plate (102), and the first beam (104a) of each of the plurality of flexible beam assemblies (104) to the ring member (103). When the ring member (103) rotates the first beam (104a) of each of the flexible beam assembly move with respect to the corresponding second beam (104b) of each of the flexible beam assembly (104). There may be a power source such as a battery (not shown in the figure) to supply the necessary power to the actuator (108) which applies torque to the ring member (103) to achieve circumferential motion. The mechanism (100) may be configured to apply a minimum force of 5 N (5 Newton) on the simulation endoscope (101). Thus, the input torque applied through the actuator (108) that produces 5 N contact force should be within the maximum torque developed by the actuator (108) of 170 mNm (milli Newton meter).

Referring back to FIG. 2, the plurality of flexible beam assemblies (104) are arranged circularly in the form of a polar array. Each of the plurality of flexible beam assemblies (104) comprises a first beam (104a) and a second beam (104b). The first beam (104a) is connectable to the ring member (103) and the second beam (104b) is connectable to the support plate (102). The second beam (104b) may be connected to the support plate (102) through a fastener such as but not limiting to pin. The first beam (104a) and the second beam (104b) are configured in a curved shape projecting radially inward forming a common joining point. The joining point of the first beam and second beam of each of the plurality of flexible beams (104) is configured as support region (106), and at least one gripping pad (107) is provided at the support region (106).

The gripping pads (107) are configured to hold and support the simulation endoscope (101) during its insertion. The plurality of flexible beam assemblies (104) may be made of pre-determined dimensions. The dimensions may be selected based on the force to be applied to the simulation endoscope (101).

Figure 4A:
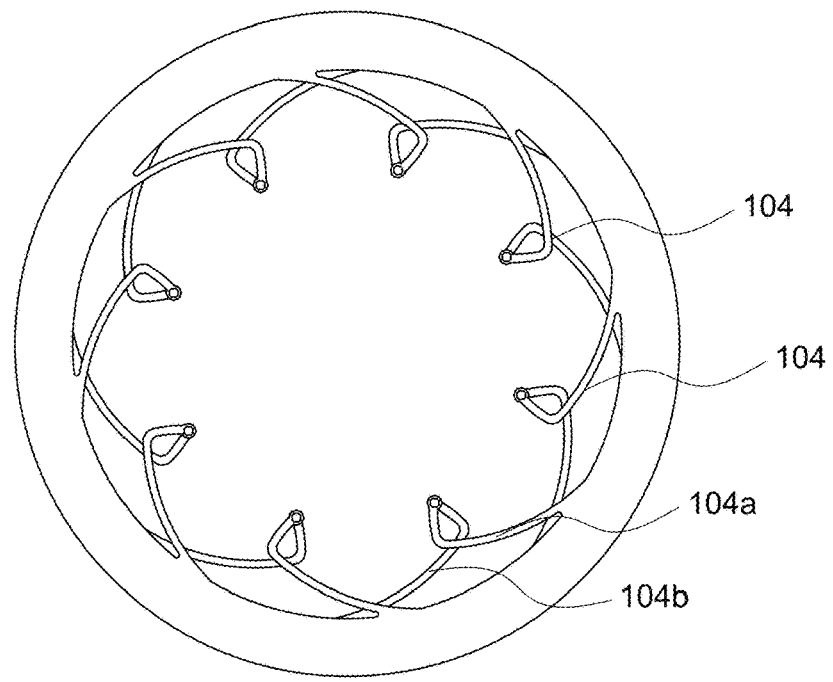
FIG. 4a and FIG. 4b illustrate schematic front view and perspective views of ring member with flexible beam assemblies of the complaint mechanism of FIG. 1.
Figure 4B:
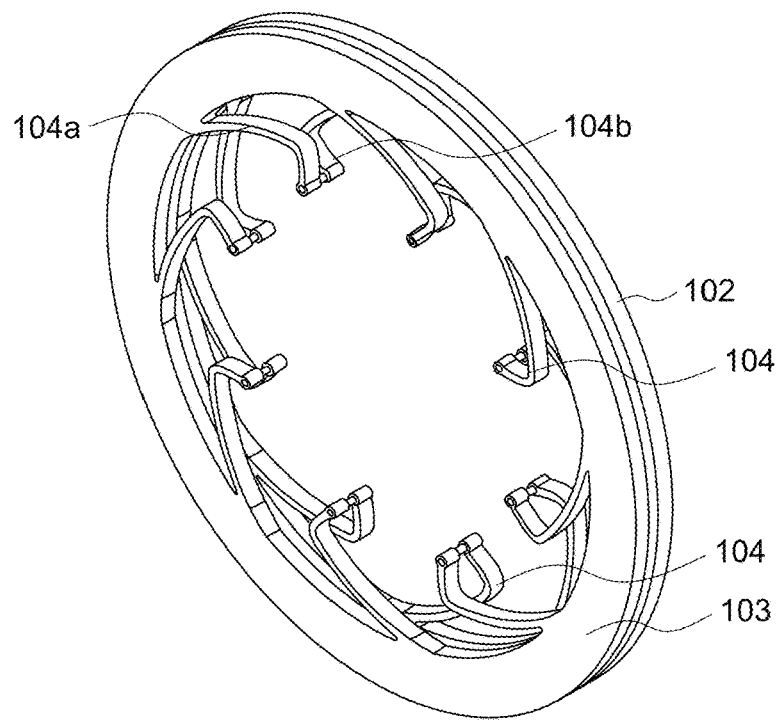

Now referring to FIG. 4a and FIG. 4b which illustrates an alternate configuration of the flexible beam assemblies. As shown in FIG. 4a and FIG. 4b, a first beam (104a) of the plurality of flexible beams (104) is connected to the ring member (103) and a second beam (104b) is connected to a support member (102). The support member (102) may be configured as a ring and may be coupled to at least one actuator. When the ring member (103) is circumferentially actuated, the ring member (103) and the support member (102) move relatively to each other and causes the radial inward motion of the plurality of flexible beam assemblies (104) for applying radial resistance on the simulation endoscope (101). Although, the different structural design of the flexible beam assemblies (104) are depicted, functions of beam assemblies (104) remain the same and are configured to apply radial resistance on the simulation endoscope. However, it is to be understood that a person skilled in the art may design the flexible beam assemblies (104) in a way different from as depicted in FIG. 4a and FIG. 4b without altering the scope of its purpose. The present disclosure is intended to cover all such variations and thus the design of flexible beam assemblies (104) depicted in FIG. 4a and FIG. 4b should not be construed as a limitation.

Figure 5:
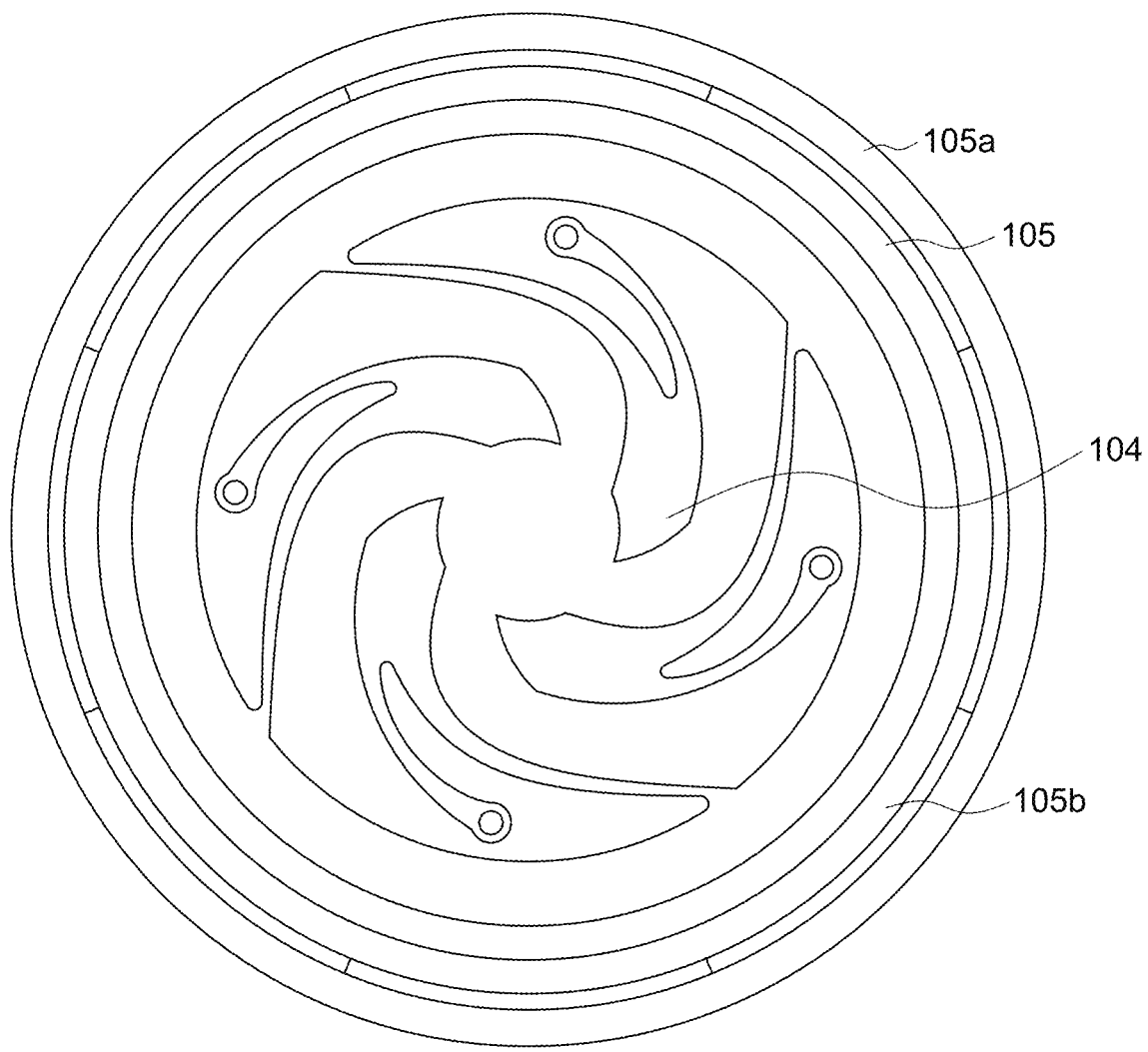
FIG. 5 illustrates a front view of the ring member and flexible beam assemblies of the complaint mechanism of FIG. 2 mounted on support plate through a bearing.

FIG. 5 illustrates mounting of the ring member (103) on the support plate (102) through a bearing (105). As shown in FIG. 5, an outer race of the bearing (105a) is fixed to the support plate (102) and an inner race of the bearing (105b) accommodates the ring member (103). The bearing (105) is configured to maintain planarity condition of the compliant mechanism (100), ensuring a reduction in tilting of the mechanism (100) during its operation. A deep groove ball-bearing may be used to constrain axial drift of the mechanism (100). The bearing (105) allows smooth circumferential motion of the mechanism (100), with restriction in axial drift. Thus, the mechanism (100) is planar, compliant and it has no axial drift.

Figure 6:
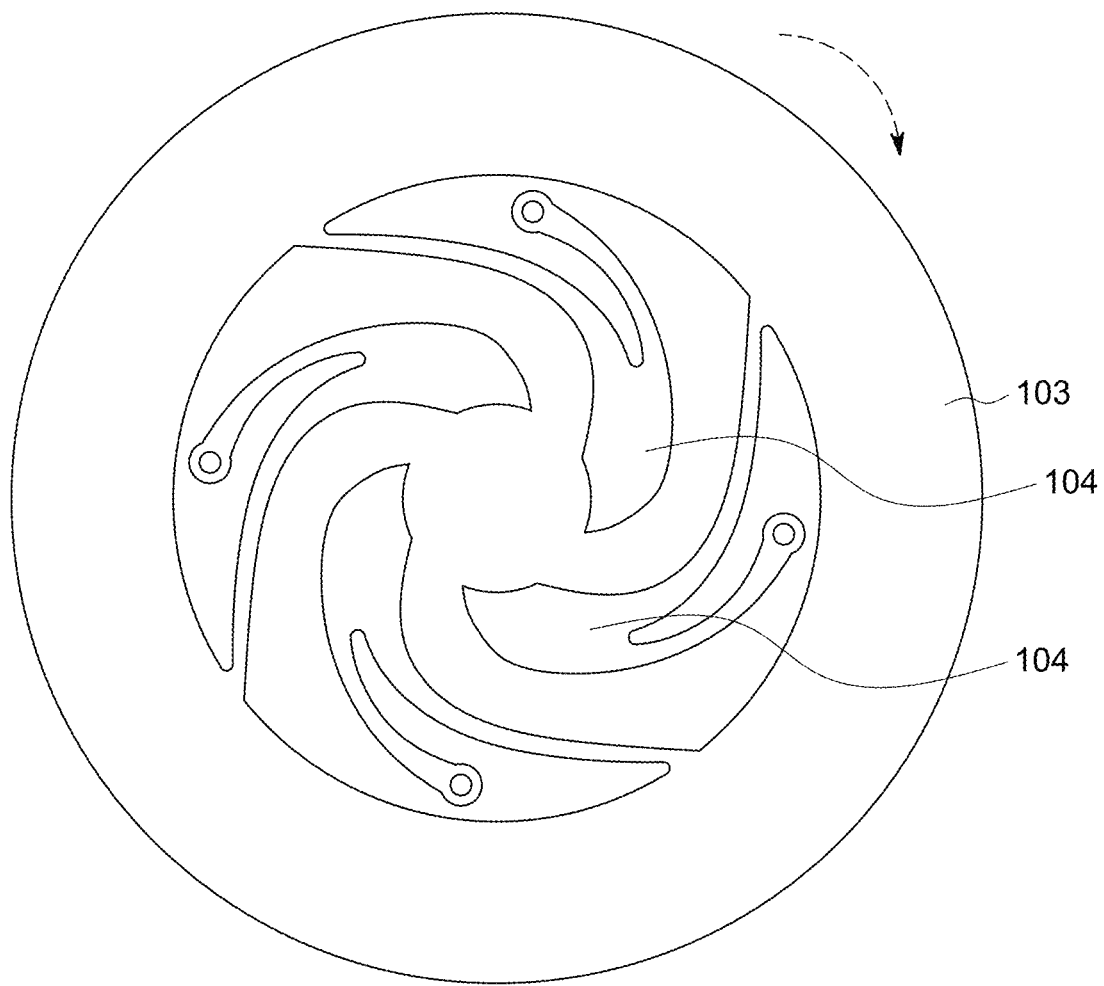

The mechanism (100) may also be configured to measure the magnitude of displacement of the flexible beams (104) when a simulation endoscope (101) is inserted. To measure the same, the mechanism (100) comprises a sensor (not shown in the figure) attached to an output shaft of the actuator (108). When the simulation endoscope (101) is inserted into the mechanism (100), the plurality of flexible beams (104) move in the radially outward direction shown in FIG. 6. This results in rotation of the ring member (103) in other direction for example in a clockwise direction. This rotation of the ring member (103) may be sensed by the sensor to measure the magnitude of displacements. Thus, the displacements sensed, measures displacement input by the user which is sensed accurately.

Figure 7:
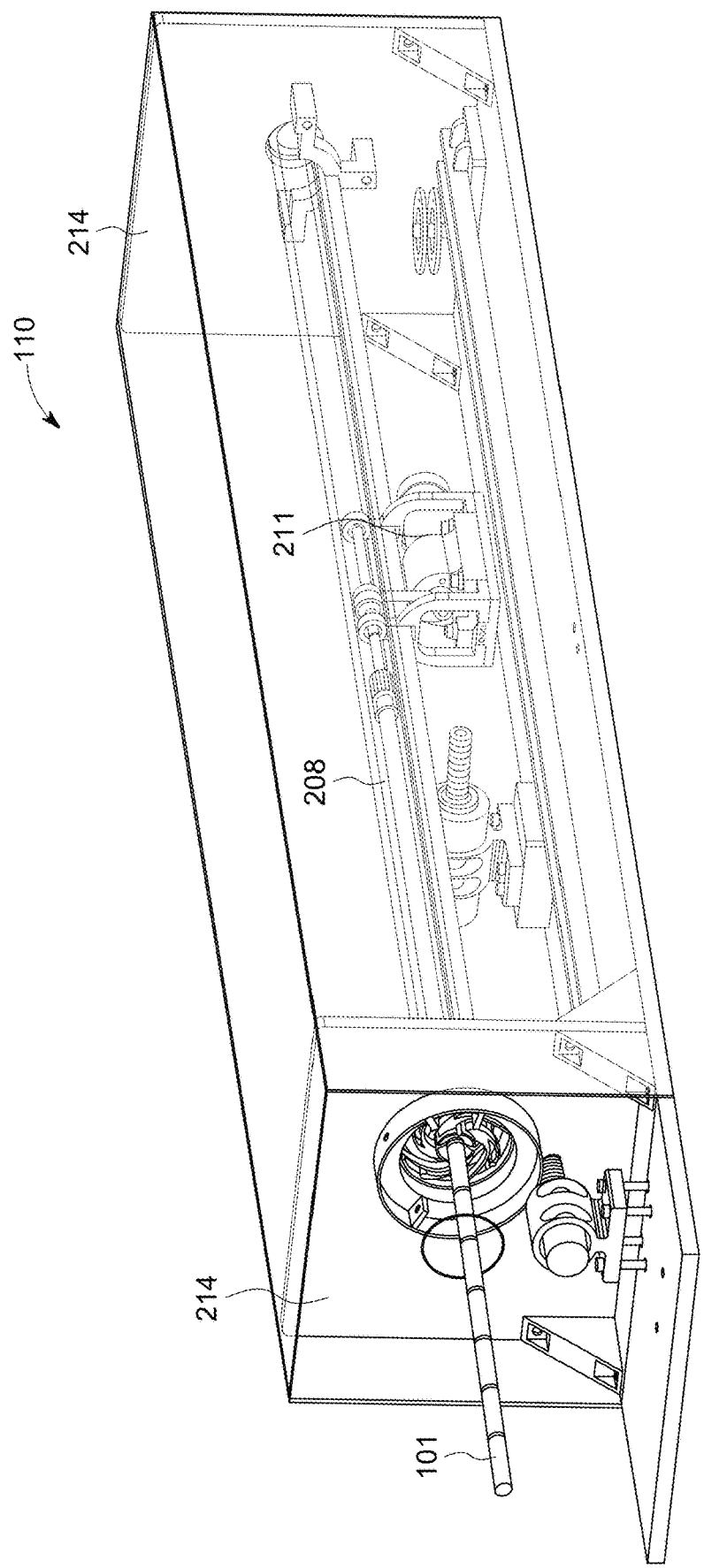
FIG. 7 illustrates a schematic representation of a device for simulating endoscopy with a compliant mechanism of FIG. 1.

FIG. 7 shows the device (110) for simulating endoscopy. The device (110) for simulating endoscopy comprises the simulation endoscope (101), and guide member (208) supported on a support frame (214). The compliant mechanism (100) is provided at the entrance of the guide member (208) and is configured to apply radial resistance on the simulation endoscope (101) to simulate the condition corresponding to encountering of the sphincter muscle. The device (110) is also configured to simulate the linear and rotary motion of the simulation endoscope (101). The device (110) may comprise a rotary actuator provisioned in the guide member (208), and mounted on a carriage (211) of the device (110). The rotary actuator is configured to apply torque on the simulation endoscope (101) to simulate the rotational movement of the simulation endoscope (101). Further, the device (110) comprises at least one linear actuator or a rotary actuator mounted on the support frame (214) and is coupled to the carriage (211). The at least one linear actuator or a rotary actuator is configured to move the carriage (211) linearly on the support frame to simulate the linear movement of the simulation endoscope (101).

It is to be understood by a person of ordinary skill in the art would do various modifications and variations without departing from the scope of the present invention. Therefore, it is intended that the present disclosure covers such modifications and variations provided they come within the ambit of the appended claims and their equivalents.

Equivalents:

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A compliant mechanism for application of radial resistance on a simulation endoscope, the mechanism comprising:
   a support plate;
   a ring member rotatably mounted on the support plate;
   a plurality of flexible beam assemblies configured in an inner circumference of the ring member, wherein, each of the plurality of flexible beam assemblies comprises:
      a first beam connectable to the ring member; and
      a second beam connectable to the support plate;
   wherein, circular motion of at least one of the support plate and the ring member, relative to each other, moves the plurality of flexible beam assemblies radially inward and radially outward to selectively apply radial resistance on the simulation endoscope.

2. The mechanism as claimed in claim 1, wherein the radial resistance is applied on the simulation endoscope when the plurality of flexible beam assemblies moves radially inward.

3. The mechanism as claimed in claim 1, wherein the ring member is mounted on the support plate through a bearing.

4. The mechanism as claimed in claim 3, wherein an outer race of the bearing is fixed to the support plate and an inner race of the bearing accommodates the ring member.

5. The mechanism as claimed in claim 1, wherein free ends of the first beam and the second beam of each of the plurality of flexible beam assemblies are interconnected to form a support region.

6. The mechanism as claimed in claim 5 comprises a gripping pad provisioned on the support region.

7. The mechanism as claimed in claim 1, wherein the plurality of flexible beam assemblies are equidistantly spaced to form a circular supporting region in the ring member.

8. The mechanism as claimed in claim 1 comprises an actuator coupled to the ring member, wherein the actuator is configured to impart circumferential actuation to the ring member.

9. The mechanism as claimed in claim 8, wherein the circumferential actuation causes rotary movement of the ring member.

10. The mechanism as claimed in claim 8 comprises a sensor coupled to the actuator.

11. The mechanism as claimed in claim 1, wherein the radial outward movement of at least one of the plurality of flexible beam assemblies impart circumferential motion to the ring member.

12. The mechanism as claimed in claim 10, wherein the sensor is configured to sense the magnitude of radially outward movement of the at least one of the plurality of flexible beam assemblies.

13. An endoscopy simulation device comprising a mechanism as claimed in claim 1.

* * * * *